(12) United States Patent
Yamano et al.

(10) Patent No.: US 8,544,329 B2
(45) Date of Patent: Oct. 1, 2013

(54) ULTRASONIC TESTING METHOD AND EQUIPMENT THEREFOR (75) Inventors: Masaki Yamano, Osaka (JP); Hiroshi Shikada, Osaka (JP); Kenji Fujiwara, Osaka (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 190 days.

(21) Appl. No.: 12/935,377

(22) PCT Filed: Mar. 27, 2009

(86) PCT No.: PCT/JP2009/056237
§ 371 (c)(1),
(2), (4) Date: Dec. 27, 2010

(87) PCT Pub. No.: WO2009/123035
PCT Pub. Date: Oct. 8, 2009

(65) Prior Publication Data
US 2011/0088476 A1 Apr. 21, 2011

(30) Foreign Application Priority Data
Mar. 31, 2008 (JP) .................................. 2008-090382

(51) Int. Cl.
*G01N 29/26* (2006.01)
*G01N 29/24* (2006.01)

(52) U.S. Cl.
USPC .............................................. 73/602; 73/622

(58) Field of Classification Search
USPC .................................................. 73/602, 622
See application file for complete search history.

(56) References Cited

U.S. PATENT DOCUMENTS

| 5,383,461 | A | * | 1/1995 | Aoki et al. ..................... 600/443 |
| 2008/0242986 | A1 | * | 10/2008 | Ichikawa ....................... 600/443 |
| 2009/0217763 | A1 | * | 9/2009 | Yamano .......................... 73/622 |
| 2009/0230822 | A1 | * | 9/2009 | Kushculey et al. ........... 310/366 |
| 2010/0274161 | A1 | * | 10/2010 | Azhari et al. ..................... 601/4 |

FOREIGN PATENT DOCUMENTS

| EP | 1918700 A1 | * | 5/2008 |
| JP | 61-223553 | | 10/1986 |
| JP | 2006-234761 | | 9/2006 |
| WO | 2007/024000 | | 3/2007 |

OTHER PUBLICATIONS

Fukuda et al., JP 55116251 A, Sep. 6, 1980, Abstract Only.*
Murayama et al., JP 59 163563 A, Sep. 14, 1984, Abstract Only.*

* cited by examiner

*Primary Examiner* — Peter Macchiarolo
*Assistant Examiner* — Rose M Miller
(74) *Attorney, Agent, or Firm* — Clark & Brody (57) ABSTRACT

An ultrasonic testing equipment includes an ultrasonic probe having a plurality of transducers arranged along a predetermined annular curved surface, a transmission/reception control unit that causes at least two transducers of the plurality of transducers to transmit the ultrasonic waves to and receive the same from a tubular test object and a ultrasonic testing waveform display unit which displays ultrasonic testing waveforms received by the selected transducers radially corresponding to the propagation directions of the ultrasonic waves transmitted from and received by the selected transducers. The waveform display unit displays the waveforms radially with a point of time corresponding to an echo on an incident point of the ultrasonic wave to the test object contained in the waveform as a beginning point and displays circles indicating points of time corresponding to the echo on the internal surface and/or the external surface of the test object around the beginning point.

2 Claims, 8 Drawing Sheets

ULTRASONIC TESTING METHOD AND EQUIPMENT THEREFOR

BACKGROUND OF THE INVENTION

1. Field of the Invention

The present invention relates to an ultrasonic testing method and an ultrasonic testing equipment for detecting a flaw existing on a tubular test object such as a steel pipe or tube (hereinafter referred to as "pipe" when deemed appropriate) using an ultrasonic wave. Particularly, the present invention relates to an ultrasonic testing method and an ultrasonic testing equipment capable of evaluating the position of a tilted flaw in the thickness direction of a tubular test object and the tilt angle of the tilted flaw easily when flaws having various tilt angles (tilted flaws) with respect to an axial direction of a tubular test object are detected manually, and also relates to an ultrasonic testing equipment capable of obtaining a high reliability test result without any change in the posture of a ultrasonic probe with respect to the tubular test object when the flaws are detected manually.

2. Description of the Related Art

As demand for higher quality pipes grows in recent years, there is an increasing trend that nondestructive test standards for the pipes are becoming more stringent.

For example, a seamless pipe, which is a typical pipe, is manufactured by punching a billet with a piercer to form a hollow shell and rolling the hollow shell with a mandrel mill or the like. The seamless pipe has flaws having various tilt angles (hereinafter referred to as "tilted flaws" when deemed appropriate) with respect to the axial direction.

A tilted flaw is believed to be caused by deformation in the axial direction of a longitudinal crack originally existing on the billet in the above manufacturing process or transfer of a flaw existing on a guide face of a guide shoe for maintaining a path center of a hollow shell. Therefore, the tilt angle of the tilted flaw with respect to the axial direction of the seamless pipe changes depending on a difference in a pipe diameter of the seamless pipe or a cause for occurrence thereof. That is, there are tilted flaws with various tilt angles on the seamless pipe.

Since there is a trend of tighter service conditions of the seamless pipes from year to year, higher quality is demanded and accurate detection of the above tilted flaws is also sternly demanded.

Conventionally, various methods for detecting the tilted flaws existing on the seamless pipes have been proposed.

In Patent Literature 1 (Japanese Unexamined Patent Publication No. 55-116251), for example, a method for detecting a tilted flaw by arranging an ultrasonic probe at an appropriate position and tilt angle depending on the position and tilt angle of the tilted flaw to be detected is proposed.

However, the method described in Patent Literature 1 has a problem that extremely much time and manpower are needed because the tilt angle of the ultrasonic probe must be changed each time in accordance with the tilt angle of the tilted flaw to be detected. Also, to detect tilted flaws with various tilt angles existing on the seamless pipe in one round of flaw-detecting work, as described above, many ultrasonic probes must be provided, each of which is arranged with a different tilt angle. That is, there are problems that large equipment is required and soaring costs are entailed, in addition to complicated arrangements/settings and calibration of ultrasonic probes.

To solve the problems of the method described in the above Patent Literature 1, a flaw detecting method that applies an ultrasonic probe array in which a plurality of transducers (elements for transmitting/receiving ultrasonic waves) are arranged in a single row is proposed in Patent Literature 2 (Japanese Unexamined Patent Publication No. 61-223553). More specifically, transversal ultrasonic waves are propagated within the pipe by aligning an arrangement direction of the transducers with the axial direction of the pipe and arranging the ultrasonic probe decentralized from an axial center of the pipe. Then, according to this method, the tilted flaws with the various tilt angles are detected by changing the tilt angle (tilt angle with respect to the axial direction of the pipe) of ultrasonic waves transmitted and received by the ultrasonic probe using electronic scanning that electrically controls transmission/reception timing of the ultrasonic wave by each transducer.

However, two main problems (first problem and second problem) shown below exist in the method described in Patent Literature 2.

<First Problem>

According to the method described in Patent Literature 2, the intensities of echoes from tilted flaws are different even if they are the tilted flaws of the same size, depending on the tilt angles of the tiled flaws. The reason is that even if the tilt angle of ultrasonic wave is changed by electronic scanning corresponding to the tilt angle of each tilted flaw such that the extension direction of the tilted flaw and a propagation direction (propagation direction viewed from a normal direction of a tangential plane of the pipe including an incident point of the ultrasonic wave) of the ultrasonic wave transmitted by the ultrasonic probe are orthogonal to each other, an external refraction angle (incident angle to an external surface flaw existing on the external surface of the pipe) and an internal refraction angle (incident angle to an internal surface flaw existing on the internal surface of the pipe) are changed corresponding to the tilt angle of each tilted flaw (corresponding to the propagation direction of the ultrasonic wave). If the intensities of the echoes from the tilted flaws are different depending on the tilt angle of the tilted flaw, there is a possibility that the detection of a harmful flaw may be prevented or minute flaws that need not to be detected may be over-detected.

<Second Problem>

If electronic scanning for electrically controlling transmission/reception timing of the ultrasonic wave by each transducer of an ultrasonic probe array described in Patent Literature 2 is used to change the tilt angle of the ultrasonic wave transmitted and received by the ultrasonic probe, electronic scanning must be repeated as many times as required depending on the tilt angle of the tilted flaw to be detected in a specific area of the pipe. That is, for example, to detect three tilted flaws with different tilt angles, electronic scanning must be repeated three times in the specific area of the pipe, and flaw-detection efficiency is reduced to ⅓ when compared with detection of flaws with a unidirectional tilt angle. As described above, the method described in Patent Literature 2 has the problem that the flaw-detection efficiency goes down as the number of the tilt angles of the tilted flaws to be detected increases.

In Patent Literature 3 (Japanese Unexamined Patent Publication No. 59-163563), on the other hand, a method for causing the ultrasonic wave to enter in any direction using a group of transducers arranged in a matrix state in order to detect the tilted flaws with the various tilt angles is proposed. More concretely, an incident direction of the ultrasonic wave is arbitrarily changed by selecting an appropriate number of arbitrary transducers from the group of transducers and by performing electronic scanning for electrically controlling transmission/reception timing (driving time) thereof. Then, it is disclosed that patterns to change the incident directions of the ultrasonic wave are stored in advance as a program.

However, the first problem that echo intensity changes in accordance with the tilt angle of each tilted flaw, as described above, is not mentioned in Patent Literature 3 and further, in order to solve the problem, nothing is disclosed about which change pattern should be used to change the incident directions of the ultrasonic wave. In addition, there is a problem similar to the second problem of the method described in Patent Literature 2. That is, there is the problem that the flaw-detection efficiency decreases because electronic scanning must be repeated as many times as the number of tilt angles of the tilted flaws to be detected.

In views of the above-described problems of the related art, the inventors of the present invention have proposed an ultrasonic testing method described in Patent Literature 4 (WO 2007/024000).

More specifically, Patent Literature 4 has proposed an ultrasonic testing method including the steps of; arranging an ultrasonic probe having a plurality of transducers so as to face a tubular test object; and causing transducers appropriately selected from the plurality of transducers to transmit and receive ultrasonic waves so that the ultrasonic waves are propagated in the tubular test object in a plurality of different propagation directions, in which an ultrasonic testing condition by the ultrasonic probe is set so that respective external refraction angles θr of ultrasonic waves in the plurality of the propagation directions are approximately equivalent and/or respective internal refraction angles θk of ultrasonic waves in the plurality of the propagation directions are approximately equivalent (claim 1 and the like of Patent Literature 4).

The ultrasonic probe has the plurality of transducers arranged along an annular curved surface obtained by cutting a predetermined spheroid with two parallel planes facing to each other that do not pass through the center of a spheroid and do not sandwich the center of the spheroid, the two parallel planes being orthogonal to the rotational axis of the spheroid, in the step of arranging the ultrasonic probe so as to face the tubular test object, the ultrasonic probe is arranged so that a longer axis direction of the ultrasonic probe is along an axial direction of the tubular test object, a shorter axis direction of the ultrasonic probe is along a circumferential direction of the tubular test object, and the center of the spheroid correctly faces an axial center of the tubular test object, and a shape of the annular curved surface is determined so that the respective external refraction angles θr of the ultrasonic wave in the plurality of propagation directions are approximately equivalent, and/or the respective internal refraction angles θk of the ultrasonic wave in the plurality of propagation directions are approximately equivalent. (claim 5 and the like of Patent Literature 4).

According to the method described in Patent Literature 4, a plurality of the tilted flaws respectively extending in a direction orthogonal to the plurality of the propagation directions can be detected with high precision. Further, the plurality of flaws can be detected rapidly by transmitting and receiving the ultrasonic waves approximately simultaneously in the plurality of different propagation directions.

Because in-line inspection for inspecting flaws in a sequence of pipe manufacturing processes may be carried out by evaluating to see whether or not there exists any flaw larger than a predetermined dimension rapidly, this can be carried out sufficiently if the ultrasonic testing method proposed by the inventors of the present invention in Patent Literature 4.

On the other hand, a pipe determined to contain flaws in the in-line inspection needs to be inspected again. This reinspection needs to evaluate not only whether or not there exists any flaw but also the position of the flaw in the thickness direction of the pipe (internal surface, external surface, central portion in the thickness direction and the like) and the tilt angle of a tilted flaw in detail by performing flaw detection manually by a qualified inspector.

Although it is demanded upon the aforementioned reinspection that an inspector can evaluate the position and the tilt angle of the flaw easily, Patent Literature 4 has not proposed any solving means for this point. Further, although it is demanded that upon scanning with the ultrasonic probe manually, the posture of the ultrasonic probe with respect to the tubular test object is not changed and a high reliability flaw detection result can be obtained, Patent Literature 4 has not proposed any solving means for this point.

SUMMARY OF THE INVENTION

The present invention has been devised to solve the above problems of the related art and an object of the present invention is to provide an ultrasonic testing method and an ultrasonic testing equipment capable of evaluating the position of a tilted flaw in a thickness direction of a tubular test object and the tilt angle of the tilted flaw easily upon manually detecting the flaws (tilted flaws) having various tilt angles with respect to an axial direction of the tubular test object and an ultrasonic test equipment capable of obtaining a high reliability flaw detection result without any change in the posture of the ultrasonic probe with respect to the tubular test object upon detecting for the flaw manually.

In order to achieve the object, the ultrasonic testing method of the present invention includes following steps (1) to (3).

(1) A step of arranging an ultrasonic probe having a plurality of transducers arranged along an annular curved surface obtained by cutting a predetermined spheroid with two parallel planes facing to each other that do not pass through the center of the spheroid and do not sandwich the center of the spheroid, the two parallel planes being orthogonal to a rotational axis of the spheroid, so as to face a tubular test object so that a longer axis direction of the ultrasonic probe is along an axial direction of the tubular test object, a shorter axis direction of the ultrasonic probe is along a circumferential direction of the tubular test object and the center of the spheroid correctly faces to the axial center of the tubular test object.

(2) A step of causing transducers appropriately selected from the plurality of the transducers to transmit and receive ultrasonic waves so that the ultrasonic waves are propagated in the tubular test object in a plurality of different propagation directions.

(3) A step of displaying ultrasonic testing waveforms received by the selected transducers radially corresponding to the propagation directions of the ultrasonic waves transmitted and received by the selected transducers.

Then, the shape of the annular curved surface is determined so that respective external refraction angles of the ultrasonic wave in the plurality of propagation directions are approximately equivalent and/or respective internal refraction angles of the ultrasonic wave in the plurality of propagation directions are approximately equivalent.

The present invention uses the ultrasonic probe having a plurality of transducers arranged along an annular curved surface obtained by cutting a predetermined spheroid with two parallel planes facing to each other that do not pass through the center of the spheroid and do not sandwich the center of the spheroid, the two parallel planes being orthogonal to a rotational axis of the spheroid. Consequently, the ultrasonic wave transmitted from each transducer is propagated toward the center of the spheroid. Further according to the present invention, the ultrasonic probe is arranged so as to face to the tubular test object so that a longer axis direction of the ultrasonic probe is along an axial direction of the tubular test object, a shorter axis direction of the ultrasonic probe is along a circumferential direction of the tubular test object and the center of the spheroid correctly faces to the axial center of the tubular test object. As a result, an elevation angle of each transducer viewed from the center of the spheroid is different depending on a position where each transducer is arranged and consequently, the angle of incidence of the ultrasonic wave transmitted from each transducer with the tubular test object will also be different. Therefore, by setting the shape (annular curved surface shape) of the ultrasonic probe appropriately, it becomes possible to cause the propagation direction of the ultrasonic wave transmitted from each transducer and the extension direction of the flaw to be detected to be orthogonal to each other and, at the same time, to maintain the external refraction angle and/or the internal refraction angle approximately constant.

If the shape of the annular curved surface is determined so that the external refraction angles of the ultrasonic waves in the plurality of the propagation directions are approximately equivalent, an approximately equivalent echo intensity can be obtained about the external surface flaw regardless of any one of the plurality of the propagation directions. Further, if the shape of the annular curved surface is determined so that the internal refraction angles of the ultrasonic waves in the plurality of the propagation directions are approximately equivalent, an approximately equivalent echo intensity can be obtained about the internal surface flaw regardless of any one of the plurality of the propagation directions. Further, if the shape of the annular curved surface is determined so that both the external refraction angle and the internal refraction angle of the ultrasonic waves in the plurality of the propagation directions are approximately equivalent, an approximately equivalent echo intensities can be obtained about the external surface flaw and the internal surface flaw regardless of any one of the plurality of the propagation directions. Thus, a plurality of flaws (external surface flaw and/or internal surface flaw) respectively extending in directions orthogonal to the plurality of the propagation directions can be detected with high precision.

According to the present invention, the ultrasonic testing waveforms received by the selected transducers are displayed radially corresponding to the propagation directions of the ultrasonic waves transmitted and received by the selected transducers. As a result, by checking the direction of the ultrasonic testing waveform containing the echo from the displayed tilted flaw visually, the tilt angle of the tilted flaw (the direction orthogonal to the direction of the displayed ultrasonic testing waveform corresponds to the tilt angle) can be evaluated easily.

Further, by checking to see in which point of time of the ultrasonic testing waveforms displayed radially an echo from the tilted flaw is contained visually, the position of the tilted flaw (internal surface, external surface, central portion in the thickness direction and the like) in the thickness direction of the tubular test object can be evaluated easily.

According to the ultrasonic testing method of the present invention, as described above, the tilted flaws having various tilt angles with respect to the axial direction of the tubular test object can be detected with high precision and at the same time, the position of the tilted flaw and the tilt angle of the tilted flaw in the thickness direction of the tubular test object can be evaluated easily.

In the meantime, "the plurality of the transducers arranged along the annular curved surface" mentioned in the present invention includes not only a case where the respective transducers (vibration surfaces of respective transducers) are formed in a curved surface so that their shape agrees with part of an annular curved surface but also a case where the respective transducers (vibration surfaces of the respective transducers) are formed in a plane and arranged in contact with the annular curved surface.

"The center of the spheroid correctly faces the axial center of the tubular test object" means that a straight line (similar to a rotational axis of the spheroid) that passes through the center of the spheroid and are orthogonal to the two parallel planes passes through the axial center of the tubular test object.

The "spheroid" is used as a terminology which includes a sphere whose a longer axis and shorter axis are identical to each other.

The "propagation direction of the ultrasonic wave" means the propagation direction of the ultrasonic wave viewed from the normal direction of a tangential plane of the tubular test object including an incident point of the ultrasonic wave.

Figure 2A:
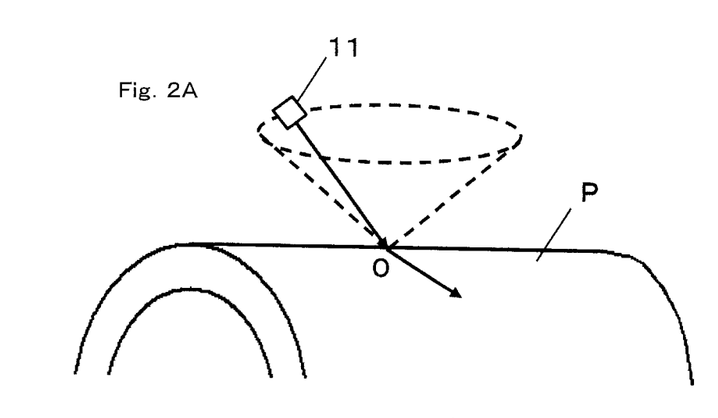
FIG. 2A is a perspective view thereof.
Figure 2B:
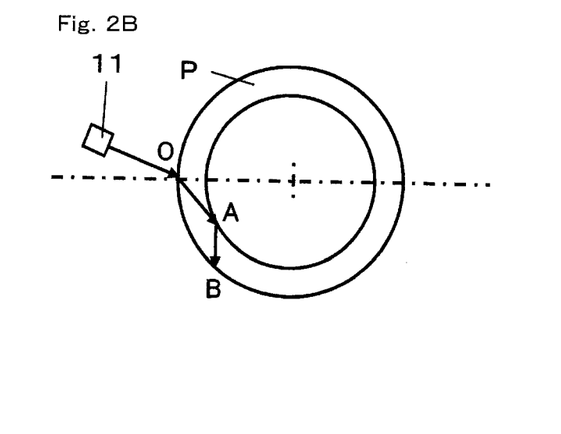
FIG. 2B is a sectional view in a circumferential direction of a pipe.
Figure 2C:
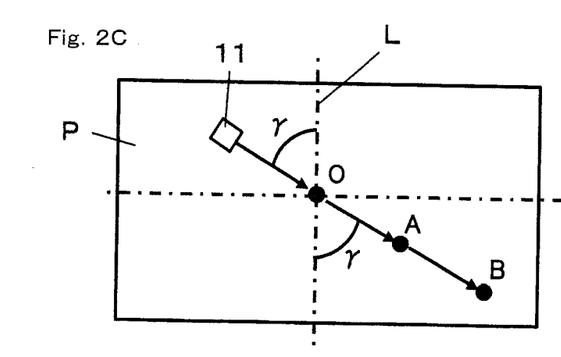
FIG. 2C is a plan view thereof and FIG. 2D is a sectional view along the ultrasonic wave propagation plane (plane containing a point O, point A and point B shown in FIG. 2B)
Figure 2D:
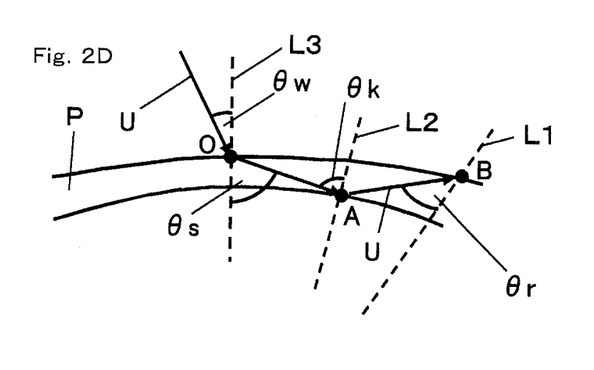

The "external refraction angle" means the angle $\theta r$ formed, on a propagation plane of the ultrasonic wave of the tubular test object P, by a normal L1 of the tubular test object P and the ultrasonic wave U (central line of an ultrasonic wave beam) at a point B on the external surface of the tubular test object P reached by the ultrasonic wave U (central line of the ultrasonic wave beam) after entering the tubular test object P (see FIG. 2D).

The "internal refraction angle" means the angle $\theta k$ formed, on the propagation plane of the ultrasonic wave of the tubular test object P, by a normal L2 of the tubular test object P and the ultrasonic wave U (central line of the ultrasonic wave beam) at a point A on the internal surface of the tubular test object P reached by the ultrasonic wave U (central line of the ultrasonic wave beam) after entering the tubular test object P (see FIG. 2D).

The "respective external (or internal) refraction angles of the ultrasonic wave in the plurality of propagation directions are approximately equivalent" means that external (or internal) refraction angles have a range of variation of up to 10°.

In the step of displaying the ultrasonic testing waveforms radially, it is preferred that the ultrasonic testing waveforms be displayed radially with a point of time corresponding to an echo on an incident point of the ultrasonic wave to the tubular test object contained in the ultrasonic testing waveform as a beginning point, and circles indicating points of time corresponding to the echoes on the internal surface and/or the external surface of the tubular test object around the beginning point be displayed.

According to such a preferred configuration, the ultrasonic testing waveforms are displayed radially and further, circles indicating points of time corresponding to the echoes on the internal surface and/or the external surface of the tubular test object are displayed. Consequently, by checking at which point of time in the ultrasonic testing waveforms displayed radially the echo from the tilted flaw is contained with the displayed circles visually (by evaluating a positional relationship between the point of time containing the echo from the tilted flaw and the circles), the position of the tilted flaw in the thickness direction of the tubular test object can be evaluated more easily.

In order to achieve the object, the present invention also provides an ultrasonic testing equipment including an ultrasonic probe having a plurality of transducers arranged along an annular curved surface obtained by cutting a predetermined spheroid with two parallel planes facing to each other that do not pass through the center of the spheroid and do not sandwich the center of the spheroid, the two parallel planes being orthogonal to a rotational axis of the spheroid, the ultrasonic probe being arranged so as to face a tubular test object so that a longer axis direction of the ultrasonic probe is along an axial direction of the tubular test object, a shorter axis direction of the ultrasonic probe is along a circumferential direction of the tubular test object and the center of the spheroid correctly faces to the axial center of the tubular test object; a transmission/reception control unit that causes at least two transducers selected from the plurality of the transducers to transmit the ultrasonic waves to and receive the same from the tubular test object; and a ultrasonic testing waveform display unit that displays ultrasonic testing waveforms received by the selected transducers radially corresponding to the propagation directions of the ultrasonic waves transmitted and received by the selected transducers.

Preferably, the ultrasonic testing waveform display unit displays the ultrasonic testing waveforms radially with a point of time corresponding to an echo on an incident point of the ultrasonic wave to the tubular test object contained in the ultrasonic testing waveform as a beginning point and displays circles indicating points of time corresponding to the echoes on the internal surface and/or the external surface of the tubular test object around the beginning point.

In order to achieve the object, the present invention further provides an ultrasonic testing equipment for detecting a flaw by ultrasonic waves in a tubular test object, including: an ultrasonic probe; a pair of follow-up mechanisms arranged along an axial direction of the tubular test object so that the ultrasonic probe is sandwiched, and connected to the ultrasonic probe; and a pair of arm mechanisms arranged along the circumferential direction of the tubular test object so that the ultrasonic probe and the follow-up mechanisms are sandwiched, and connected to the ultrasonic probe while an interval between the pair of arm mechanisms is adjustable, wherein the follow-up mechanism includes at least one rolling roller that rolls in contact with the external surface of the tubular test object, and the arm mechanism has at least one pair of rolling rollers that are arranged to sandwich the center of the ultrasonic probe and roll in contact with the external surface of the tubular test object.

The ultrasonic testing equipment of the present invention includes a pair of follow-up mechanisms which are arranged along the axial direction of the tubular test object so that the ultrasonic probe is sandwiched, and connected to the ultrasonic probe. This follow-up mechanism has at least one rolling roller which rolls in contact with the external surface of the tubular test object. Thus, the ultrasonic probe is placed on the external surface of the tubular test object via at least one rolling roller possessed by a pair of follow-up mechanism and in order to scan the external surface of the tubular test object by rolling the rolling roller.

The ultrasonic testing equipment of the present invention includes a pair of arm mechanisms which are arranged along the circumferential direction of the tubular test object so that the ultrasonic probe and the follow-up mechanisms are sandwiched, and connected to the ultrasonic probe while the interval between the pair of arm mechanisms is adjustable. The arm mechanism has at least a pair of rolling rollers that are arranged to sandwich the center of the ultrasonic probe and roll in contact with the external surface of the tubular test object. Therefore, when the tubular test object is sandwiched from the circumferential direction by means of the pair of arm mechanisms by adjusting the interval between the pair of arm mechanisms, the posture of the ultrasonic probe connected to the pair of arm mechanisms with respect to the tubular test object can be kept constant. Then, even in a condition that the tubular test object is sandwiched from the circumferential direction by the pair of arm mechanism, the ultrasonic probe can be run along the external surface of the tubular test object for scanning by rolling the rolling rollers, because each arm mechanism has the rolling rollers.

As described above, the ultrasonic testing equipment of the present invention can obtain a high reliability flaw detection result without any change in the posture of the ultrasonic probe with respect to the tubular test object.

The aforementioned ultrasonic testing equipment is particularly effective in case where the ultrasonic probe includes a plurality of the transducers arranged along the annular curved surface. That is, the ultrasonic probe has a plurality of transducers arranged along an annular curved surface obtained by cutting a predetermined spheroid with two parallel planes facing to each other that do not pass through the center of the spheroid and do not sandwich the center of the spheroid, the two parallel planes being orthogonal to a rotational axis of the spheroid, and is arranged so as to face a tubular test object so that a longer axis direction of the ultrasonic probe is along an axial direction of the tubular test object, a shorter axis direction of the ultrasonic probe is along a circumferential direction of the tubular test object and the center of the spheroid correctly faces to the axial center of the tubular test object. The ultrasonic testing equipment preferably includes a transmission/reception control unit that causes at least two transducers selected from the plurality of the transducers to transmit the ultrasonic waves to and receive the same from the tubular test object.

According to such a preferred configuration, not only the tilted flaws can be detected with high precision but also the posture of the ultrasonic probe with respect to the tubular test object is not changed, thereby obtaining a high reliability flaw detection result.

More preferably, the ultrasonic testing equipment includes a ultrasonic testing waveform display unit that displays ultrasonic testing waveforms received by the selected transducers radially corresponding to the propagation directions of the ultrasonic waves transmitted and received by the selected transducers.

According to such a preferred configuration, there is a further advantage that not only the position of the tilted flaw in the thickness direction of the tubular test object but also the tilt angle of the tilted flaw can be evaluated easily.

Preferably, the ultrasonic testing waveform display unit displays the ultrasonic testing waveforms radially with a point of time corresponding to an echo on an incident point of the ultrasonic wave to the tubular test object contained in the ultrasonic testing waveform as a beginning point and displays circles indicating points of time corresponding to the echoes on the internal surface and/or the external surface of the tubular test object around the beginning point.

According to such a preferred configuration, the position of the tilted flaw in the thickness direction of the tubular test object can be evaluated more easily.

According to the present invention, when the tilted flaws having various tilt angles with respect to the axial direction of the tubular test object are detected manually, the position of the tilted flaw in the thickness direction of the tubular test object and the tilt angle of the tilted flaw can be evaluated easily. Further, when detecting the flaws manually, the posture of the ultrasonic probe with respect to the tubular test object is not changed thereby obtaining a high reliability flaw detection result.

BRIEF DESCRIPTION OF THE DRAWINGS

FIGS. 1A to 1D are schematic views each illustrating the schematic configuration of an ultrasonic testing equipment according to an embodiment of the present invention.

FIGS. 2A to 2D are explanatory diagrams each showing a propagation behavior of ultrasonic wave in the ultrasonic testing equipment shown in FIGS. 1A to 1D.

FIGS. 3A to 3C are explanatory diagrams for explaining the function of the ultrasonic testing waveform display unit shown in FIGS. 1A to 1D.

FIGS. 6A to 6C are schematic views each showing the schematic configuration of a structure around a mechanical section possessed by the ultrasonic testing equipment shown in FIG. 1A to 1D.

FIGS. 8A to 8C are schematic views each showing the schematic configuration of other ultrasonic testing equipment to which the mechanical section shown in FIGS. 6A to 6C is applied.

DETAILED DESCRIPTION OF THE PREFERRED EMBODIMENTS

Hereinafter, an embodiment of the ultrasonic testing method and equipment of the present invention will be described with reference to the accompanying drawings.

Figure 1A:
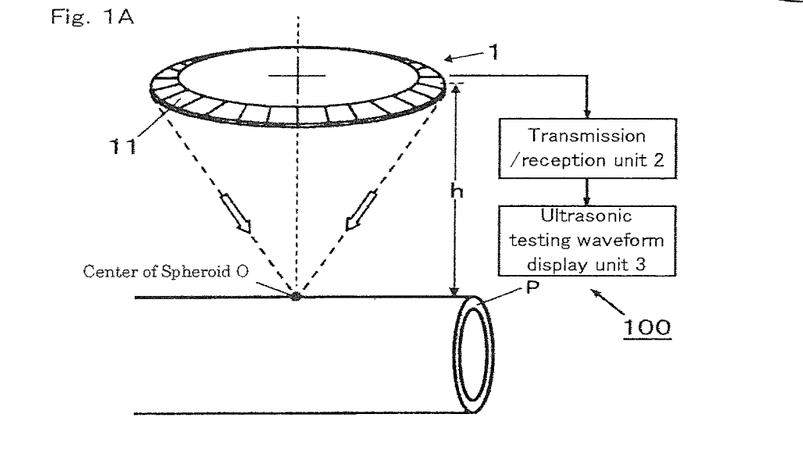
FIG. 1A is a perspective view thereof.
Figures 1B, 1C:
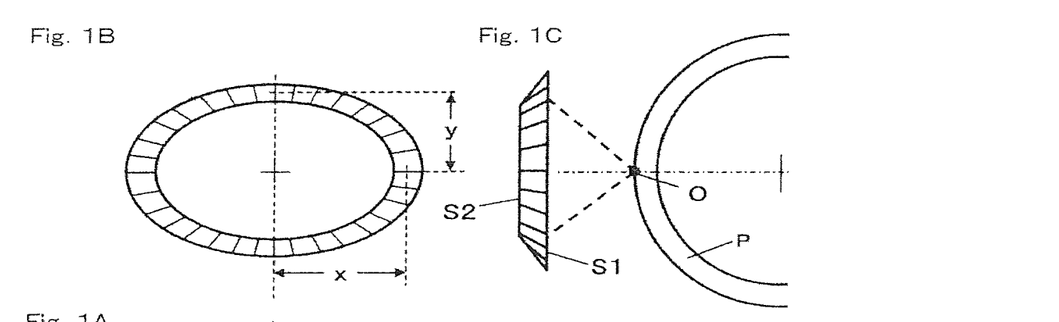
FIG. 1B is a plan view thereof.
FIG. 1C is a side view thereof and FIG. 1D is an explanatory view.
Figure 1D:
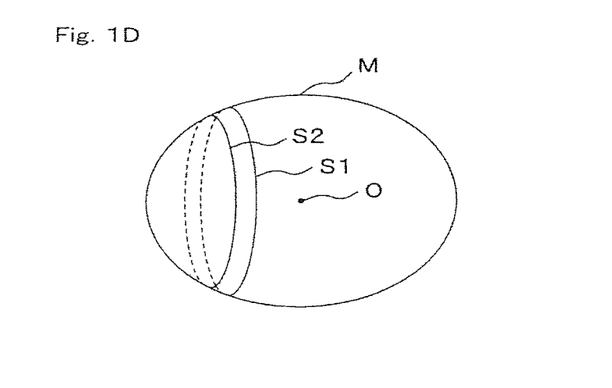

FIGS. 1A to 1D are schematic views each showing the schematic configuration of an ultrasonic testing equipment according to an embodiment of the present invention. FIG. 1A shows a perspective view, FIG. 1B shows a plan view, FIG. 1C shows a side view and FIG. 1D shows an explanatory view thereof. FIGS. 2A to 2D are explanatory diagrams each showing a propagation behavior of ultrasonic wave in the ultrasonic testing equipment shown in FIGS. 1A to 1D. FIG. 2A shows a perspective view, FIG. 2B shows a sectional view in a circumferential direction of a pipe, FIG. 2C shows a plan view and FIG. 2D shows a sectional view along the ultrasonic wave propagation plane (plane containing a point O, point A and point B shown in FIG. 2B).

As shown in FIG. 1A to 1D, the ultrasonic testing equipment 100 of this embodiment is an ultrasonic testing equipment for detecting a pipe P for any flaw using ultrasonic waves and includes an ultrasonic probe 1, a transmission/reception unit 2 for controlling transmission and reception of ultrasonic waves by the ultrasonic probe 1 and a ultrasonic testing waveform display unit 3 for displaying ultrasonic testing waveforms received by the ultrasonic probe 1. Further, the ultrasonic testing equipment 100 of this embodiment includes a mechanical section 4 (not shown in FIGS. 1A to 1D) for running the ultrasonic probe 1 on the external surface of the pipe P for scanning.

The ultrasonic probe 1 has a plurality of transducers 11 arranged along an annular curved surface. The aforementioned annular curved surface is a curved surface obtained by cutting a predetermined spheroid M with two parallel planes S1 and S2 facing to each other that do not pass through the center O of the spheroid M and do not sandwich the center O of the spheroid M, the two parallel planes being orthogonal to the rotational axis of the spheroid M (see FIG. 1C and FIG. 1D). Then, the ultrasonic probe 1 is arranged so as to face the pipe P so that a longer axis direction (direction x indicated in FIG. 1B) of the ultrasonic probe is along an axial direction of the pipe P, a shorter axis direction (direction y indicated in FIG. 1B) of the ultrasonic probe is along a circumferential direction of the pipe P and the center O of the spheroid M correctly faces an axial center of the pipe P.

The transmission/reception control unit 2 of this embodiment includes a transmission circuit, a reception circuit and a control circuit. The transmission circuit includes pulsers which are connected to each transducer 11 in order to supply a pulse signal for making each transducer 11 send ultrasonic waves and a delay circuit A for setting a delay time of the pulse signal supplied to each transducer 11 by each pulser. The reception circuit includes receivers which are connected to each transducer 11 in order to amplify the ultrasonic testing waveform received by each transducer 11 and a delay circuit B for setting a delay time of the ultrasonic testing waveform amplified by each receiver. The control circuit selects a transducer 11 for transmitting/receiving ultrasonic waves from a plurality of the arranged transducers 11 and operates to determine the delay times to be set by the delay circuit A or the delay circuit B for each of the selected transducers 11.

The transmission/reception control unit 2 having the above-described configuration selects at least two or more transducers 11 from the plurality of the transducers 11 in order to transmit ultrasonic waves from the selected transducer 11 to the pipe P and then receive the reflected ultrasonic wave from the pipe P.

Hereinafter, a specific method for determining the shape (annular curved surface shape) of the ultrasonic probe 1 will be described with reference to FIGS. 2A to 2D. When determining the shape of the ultrasonic probe 1, as shown in FIGS. 2A to 2D, a state is considered in which the ultrasonic probe 1 is arranged so that the center O of the spheroid M is located in the vicinity of the external surface of the pipe P (consequently, ultrasonic wave transmitted from each transducer 11 impinges upon the pipe P with the aforementioned center O set as an incident point).

As shown in FIGS. 2A to 2D, ultrasonic wave transmitted from each of the transducers 11 constituting the ultrasonic probe 1 is entered via the point O (center O of the spheroid) on the external surface of the pipe P, reflected by a point A on the internal surface of the pipe P and then reaches a point B on the external surface of the pipe P. Then, an angle (propagation angle) between a propagation direction of ultrasonic wave entered via the point O (propagation direction viewed from a normal direction of a tangential plane of the pipe P including the incident point O) and a tangential L in a circumferential direction of the pipe P passing through the incident point O is designated to be γ (hereinafter, also referred to as a "propagation direction γ" as required), an external refraction angle (angle between a normal line L1 at the point B of the pipe P and ultrasonic wave beam U on an ultrasonic wave propagation surface indicated in FIG. 2D) at the point B is referred to as θr, an internal refraction angle (angle between a normal line L2 at the point A of the pipe P and ultrasonic wave beam U on the ultrasonic wave propagation surface indicated in FIG. 2D) at the point A is referred to as θk. Further, an angle of incidence of the ultrasonic wave to the pipe P (angle between a normal line L3 at the incident point O of the pipe P and the entering ultrasonic wave beam U on an ultrasonic wave propagation surface indicated in FIG. 2D) is referred to as θw and a refraction angle of the ultrasonic wave in the pipe P (angle between the normal line L3 at the incident point O of the pipe P and the ultrasonic beam U after the ultrasonic wave beam is entered on an ultrasonic wave propagation surface indicated in FIG. 2D) is referred to as θs.

The ultrasonic wave entered in the pipe P with the angle of incidence θw indicates a geometric propagation behavior. That is, the ultrasonic wave entered into the pipe P with the angle of incidence θw is propagated in the pipe P at the angle of incidence θs determined according to the Snell's law. As introduced geometrically, the external refraction angle θr is equivalent to the refraction angle θs. That is, the following equation (7) is established.

$$\sin \theta r = V_s/V_i \cdot \sin \theta w \quad (7)$$

where, in the above equation (7), Vs means a propagation velocity of the ultrasonic wave propagated in the pipe P and Vi means a propagation velocity of the ultrasonic wave in coupling medium filled between the ultrasonic probe 1A and the pipe P.

On the other hand, the internal refraction angle θk is a function among the angle of incidence θw, the propagation angle γ and the thickness to outside diameter ratio t/D of the pipe P, as described in Patent Literature 4. The internal refraction angle θk becomes a minimum value when the propagation direction γ of the ultrasonic wave meets the axial direction of the pipe P (that is, propagation angle γ=90°) so that it is equal to the external refraction angle θr (=refraction angle θs). The internal refraction angle θk becomes a maximum value when the propagation direction γ of the ultrasonic wave meets the circumferential direction of the pipe P (that is, propagation angle γ=0°), it can be expressed by the following equation (8).

$$\theta k = \sin^{-1}\left(\frac{\sin\theta r}{1 - 2(t/D)}\right) \quad (8)$$

If the thickness to outside diameter ratio t/D of the pipe P is about several percent, a difference between the internal refraction angle θk and the external refraction angle θr calculated according to the above equation (8) falls within a range of about 10°. Thus, a difference between the internal refraction angle θk when an internal surface flaw (detected by ultrasonic wave whose propagation direction γ meets circumferential direction of the pipe P) extending in the axial direction of the pipe P is detected and the internal refraction angle θk (=θs) when the internal surface flaw (detected by ultrasonic wave whose propagation direction γ meets the axial direction of the pipe P) extending in the circumferential direction of the pipe P is detected falls within a range of about 10°, thereby producing no significant difference in detection performance between the both internal surface flaws. However, if the t/D of the pipe P is more than 15%, the internal refraction angle θk calculated according to the above equation (8) is increased by 20° or more with respect to the external refraction angle θs (that is, the internal refraction angle θk is increased by 20° or more when the propagation direction γ is changed from the axial direction of the pipe P to the circumferential direction), thereby seriously dropping the detection performance for the internal surface flaw extending in the axial direction of the pipe P. As for the internal surface flaw having a tilt angle between the axial direction and the circumferential direction of the pipe P also, the detection performance is dropped as the internal refraction angle θk is increased.

To prevent the detection performance for the flaw from being dropped by changes of the internal refraction angle θk described above, a refraction angle θs corresponding to each propagation direction γ is changed (that is, the angle of incidence θw is changed) so that the internal refraction angle θk corresponding to each propagation direction γ is of a approximately constant value, depending on the propagation direction γ of the ultrasonic wave (that is, corresponding to a tilt angle of the flaw orthogonal to the propagation direction γ of the ultrasonic wave).

The ultrasonic probe 1 of this embodiment is designed to a shape in which the angle of incidence θw corresponding to each propagation direction γ is changed so that the internal refraction angle θk corresponding to each propagation direction γ is of a approximately constant value, depending on the propagation direction γ of the ultrasonic wave transmitted from each transducer 11. As described previously, the ultrasonic probe 1 includes a plurality of the transducers 11 arranged along the annular curved surface and the aforementioned annular curved surface is a curved surface obtained by cutting a predetermined spheroid M with two parallel planes S1 and S2 (see FIG. 1C and FIG. 1D) that do not pass through the center O of the spheroid M and do not sandwich the center O of the spheroid M, the two parallel planes being orthogonal to the rotational axis of the spheroid. Consequently, the propagation direction γ of the ultrasonic wave transmitted from each transducer 11γ is in a range of −180° to 180°. The elevation angle of each transducer 11 viewed from the center O of the spheroid M is different depending on the position in which the transducer 11 is arranged. In other words, the elevation angle of the transducer 11 is determined depending on the longer axis and shorter axis of the ultrasonic probe 1 and a distance from the center O of the spheroid M of the ultrasonic probe 1 and the elevation angle is different depending on the position in which the transducer 11 is arranged (corresponding to the propagation direction γ of the ultrasonic wave transmitted form each transducer 11). An angle obtained by subtracting this elevation angle from 90° corresponds to the angle of incidence θw. Thus, the ultrasonic probe 1 of this embodiment is designed to a shape in which the angle of incidence θw corresponding to each propagation direction γ is changed by setting the longer axis and shorter axis of the ultrasonic probe 1 and the distance from the center O of the spheroid M of the ultrasonic probe 1 so that the internal refraction angle θk corresponding to the propagation direction γ is of a approximately constant value, corresponding to the propagation direction γ of the ultrasonic wave transmitted from each transducer 11.

Speaking more specifically, when it is assumed that the longer axis of the ultrasonic probe 1 is 2x, the shorter axis thereof is 2y and the distance from the center O of the spheroid M of the ultrasonic probe 1 (average distance from the center O of the spheroid M to the planes S1 and S2) is h as shown in FIGS. 1A to 1D, the angle of incidence θw (referred to as θw1) of the ultrasonic wave transmitted from the transducer 11 located at the longer axis of the ultrasonic probe 1 and the angle of incidence θw (referred to as θw2) of the ultrasonic wave transmitted from the transducer 11 located at the shorter axis of the ultrasonic probe 1 are expressed in the following equations (9) and (10).

$$\theta w1 = \tan^{-1}(x/h) \quad (9)$$

$$\theta w2 = \tan^{-1}(y/h) \quad (10)$$

The shape of the ultrasonic probe 1 (x, y and h) is determined corresponding to the t/D of a pipe P to be detected so that the angles of incidence θw1 and θw2 expressed by the above equations (9), (10) satisfy the following equations (11).

$$\sin \theta w2 = \sin \theta w1 \cdot \{1 - 2(t/D)\} \quad (11)$$

When the angles of incidence θw1 and θw2 satisfy the above equation (11), the internal refraction angle θk when the propagation direction γ of the ultrasonic wave agrees with the axial direction of the pipe P (when the transducer 11 located on the longer axis of the ultrasonic probe 1 sends the ultrasonic wave) and the internal refraction angle θk when the propagation direction γ of the ultrasonic wave agrees with the circumferential direction of the pipe P (when the transducer 11 located on the shorter axis of the ultrasonic probe 1 sends the ultrasonic wave) are approximately equal to each other as described in Patent Literature 4. Consequently, in case where the propagation direction γ of the ultrasonic wave is located between the axial direction and the circumferential direction of the pipe P, an approximately equal internal refraction angle θk is obtained. That is, even if the propagation direction γ of the ultrasonic wave is in a range of −180° to 180°, an approximately equal internal refraction angle θk can be obtained.

Because the shape of the ultrasonic probe 1 of this embodiment is determined as described above, the propagation direction γ of the ultrasonic wave transmitted from each transducer 11 can be made orthogonal to a direction in which the direction of a flaw to be detected is extended and at the same time, the internal refraction angle θk can be made approximately constant and an equal echo intensity can be obtained regardless of the tilt angle of each flaw. In this way, the transducers 11 of a number equal to that of the tilt angles of the flaws to be detected are selected by the transmission/reception control unit 2 and the ultrasonic waves are transmitted and received by the selected transducers 11, thereby the flaws having various tilt angles can be detected with high precision.

In the ultrasonic probe 1 of this embodiment, preferably the center O of the spheroid is arranged in the vicinity of the external surface of the pipe P not only when the aforementioned shape is determined but also when the flaws are detected actually.

In such a preferable equipment, the incident points of the ultrasonic wave transmitted from each of the transducers 11 to the pipe P approximately agree (the center O of the spheroid becomes an incident point). Consequently, the propagation behavior of the ultrasonic wave just like expected when the shape of the ultrasonic probe 1A is determined can be obtained (the internal refraction angle θk is approximately constant regardless of the propagation direction of the ultrasonic wave), and the flaws having various tilt angles can be detected with high precision.

The shape of the ultrasonic probe 1 of this embodiment enables the internal refraction angle θk to be approximately constant while the external refraction angle θr is changed depending on the propagation direction γ. In other words, the ultrasonic probe 1 of this embodiment is formed into a preferable shape for detecting the internal surface flaws having various tilt angles with high precision. To detect the external surface flaws having various tilt angles with high precision, the external refraction angle θr needs to be approximately constant regardless of the tilt angle of each flaw (that is, regardless of the propagation direction γ of the ultrasonic wave). Because the external refraction angle θr is equal to the refraction angle θs as described above, the refraction angle θs is made approximately constant regardless of the propagation direction γ and for this purpose, the angle of incidence θw is made approximately constant regardless of the propagation direction γ. To make the angle of incidence θw approximately constant regardless of the propagation direction γ of the ultrasonic wave, the lengths of the longer axis (2x) and the shorter axis (2y) of the ultrasonic probe are set to an approximately equal value. That is, a shape obtained when the spheroid is spherical is set up. The ultrasonic probe having such a shape enables the external refraction angle r to be approximately constant regardless of the propagation direction γ, thereby the external surface flaws having various tilt angles can be detected with high precision.

A preferable shape of the ultrasonic probe for detecting the flaw is selected depending on which the prominent test object of flaw in the pipe P is the internal surface flaw or the external surface flaw. Alternatively, if both the internal surface flaw and the external surface flaw need to be detected equally, a shape having values x, y approximately in the middle between the shape (x, y and h) of the ultrasonic probe which satisfies the equation (11) preferable for detecting the internal surface flaw and the shape of an ultrasonic probe which satisfies x=y preferable for detecting the external surface flaws is selected.

Hereinafter, functions of the ultrasonic testing waveform display unit 3 will be described with reference to FIGS. 3A to 3C.

Figure 3A:
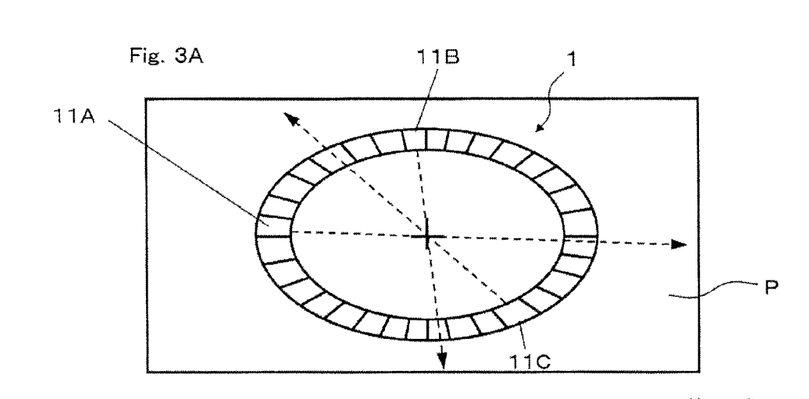
FIG. 3A shows a relationship between a selected transducer and the propagation direction of ultrasonic wave to be transmitted from the selected transducer.
Figure 3B:
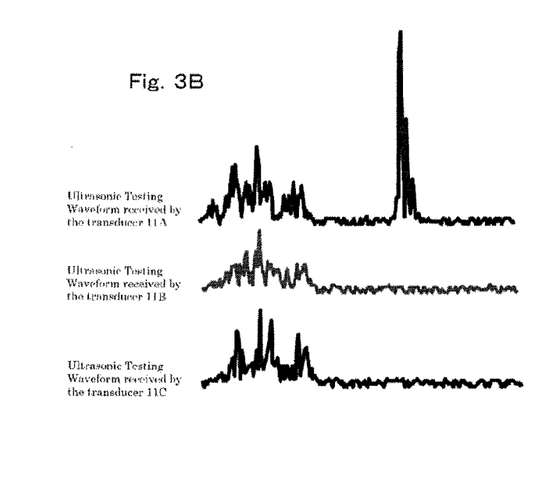
FIG. 3B shows an example of the waveform of ultrasonic wave to be received by the selected transducer.
Figure 3C:
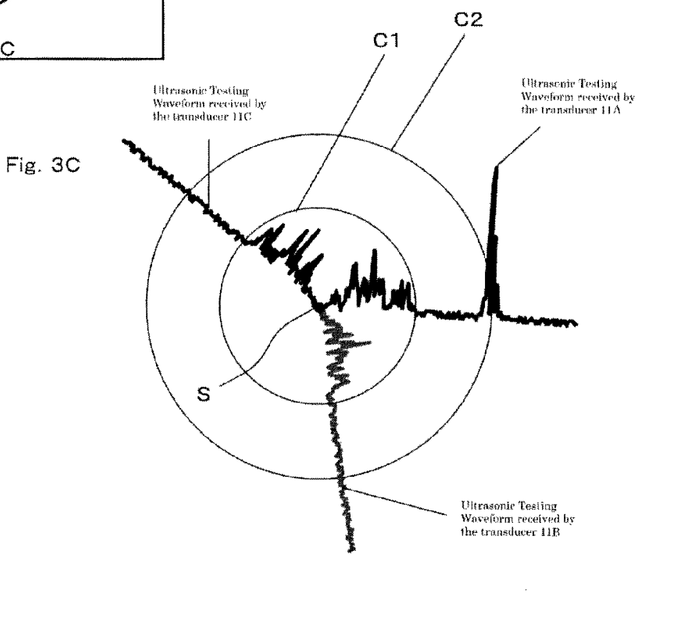
FIG. 3C shows an example of display of the waveform of the ultrasonic wave.

FIGS. 3A to 3C are explanatory diagrams for explaining the functions of the ultrasonic testing waveform display unit shown in FIGS. 1A to 1D. FIG. 3A shows a relationship between the selected transducers and the propagation directions of ultrasonic waves transmitted from the selected transducers, FIG. 3B shows an example of the ultrasonic testing waveforms received by the selected transducers and FIG. 3C shows an example of display of the ultrasonic testing waveforms. The ultrasonic testing waveform display unit 3 displays ultrasonic testing waveforms received by the selected transducers 11 corresponding to the propagation direction γ of the ultrasonic wave transmitted to and received by the selected transducers 11 (transducer 11A, 11B, 11C in the example shown in FIGS. 3A to 3C) radially.

More specifically, the ultrasonic testing waveform display unit 3 displays the ultrasonic testing waveforms radially with a point of time corresponding to an echo on an incident point of the ultrasonic wave to the pipe P contained in the ultrasonic testing waveform as a beginning point S. More specifically, the ultrasonic testing waveform display unit 3 converts each ultrasonic testing waveform received by the respective transducers 11A to 11C output form the transmission/reception control unit 2 into digital data and displays a gray image corresponding to the intensities of the ultrasonic testing waveform, a color image which is coded in different colors corresponding to the intensities of the ultrasonic testing waveform or binarized image obtained by binarizing the ultrasonic testing waveform with a predetermined threshold, on an appropriate monitor or the like.

The ultrasonic testing waveform display unit 3 displays the ultrasonic testing waveforms radially as described above and further displays circles indicating points of time corresponding to the echoes on the internal surface and/or the external surface of the pipe P around the beginning point S. The coordinates of these circles can be calculated from the thickness of the pipe P, the refraction angle θs of the ultrasonic wave in the pipe P and the propagation velocity Vs of the ultrasonic wave propagated within the pipe P. The example shown in FIGS. 3A to 3C indicates a circle C1 indicating a point of time (so-called 0.5 skip) corresponding to an echo when the ultrasonic wave entered into the pipe P reaches the internal surface of the pipe P first and a circle C2 indicating a point of time (so-called 1.0 skip) corresponding to an echo when the ultrasonic wave entered into the pipe P is reflected by the internal surface of the pipe P and then reaches the external surface of the pipe P first.

Figure 4A:
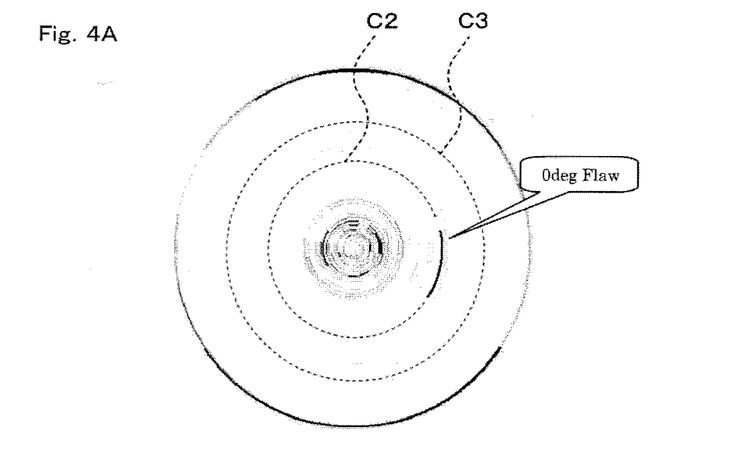
FIGS. 4A and 4B show an example that a tilted flaw generated in a steel pipe is detected using the ultrasonic testing equipment shown in FIG. 1A to 1D to display the ultrasonic testing waveforms with the ultrasonic testing waveform display unit.
Figure 4B:
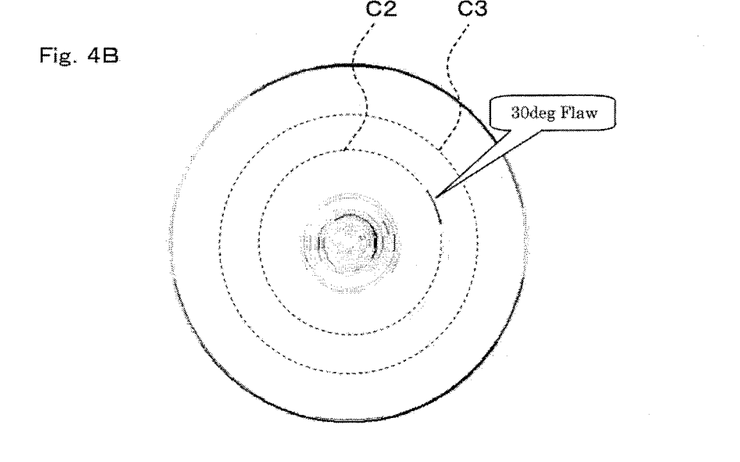

FIGS. 4A and 4B show an example that a tilted flaw generated in a steel pipe is detected using the ultrasonic testing equipment 100 of this embodiment so as to display the ultrasonic testing waveforms with the ultrasonic testing waveform display unit 3. In the meantime, the detected steel pipe for any flaw has an outside diameter of 178 mm and a thickness of 10 mm, and the shape of the ultrasonic probe 1 (annular curved surface shape) is a shape having values x, y approximately in the middle between the shape (x, y and h) of the ultrasonic probe which satisfies the equation (11) preferable for detecting the internal surface flaw and the shape of an ultrasonic probe which satisfies x=y preferable for detecting the external surface flaws. The example shown in FIGS. 4A and 4B indicates the aforementioned circle C2 and a circle C3 indicating a point of time (so-called 1.5 skip) corresponding to an echo when the ultrasonic wave entered into the pipe P is reflected in the pipe P and reaches the internal surface of the pipe P for the second time.

As shown in FIGS. 4A and 4B, the ultrasonic testing waveform display unit 3 displays the ultrasonic testing waveforms received by the selected transducers 11 radially corresponding to the propagation directions γ of the ultrasonic waves transmitted and received by the selected transducers 11. Consequently, the tilt angle (a direction orthogonal to the direction of the displayed ultrasonic testing waveform corresponds to the tilt angle) of the tilted flaw can be evaluated easily by checking the direction of the ultrasonic testing waveform containing an echo from the displayed tilt flaw visually. According to an example shown in FIG. 4A, it is possible to recognize that the tilted flaw extending orthogonally to this propagation direction exists at a position in which the propagation angle γ of the ultrasonic wave is approximately 0° easily. Further, according to an example shown in FIG. 4B, it is also possible to recognize that the tilted flaw extending orthogonally to this propagation direction exists at a position in which the propagation angle γ of the ultrasonic wave is approximately 30°.

As shown in FIGS. 4A and 4B, the ultrasonic testing waveform display unit 3 displays the ultrasonic testing waveforms radially and at the same time, the circles (C2, C3 in the example shown in FIGS. 4A and 4B) indicating a point of time corresponding to the echo on the internal surface and/or the external surface of the pipe P. By checking visually at which point of time in the ultrasonic testing waveform displayed radially any echo from the tilted flaw is contained with the displayed circles, a position of the tilted flaw in the thickness direction of the pipe P can be evaluated easily. In the examples shown in FIG. 4A and FIG. 4B, the echoes from the tilted flaw exist on the circle C2. Thus, it is possible to recognize that the tilted flaw exists on the external surface of the pipe P easily.

Figure 5A:
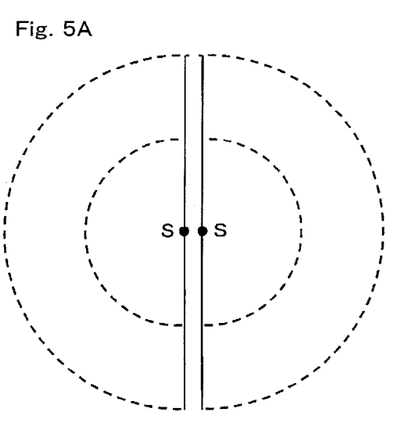
FIGS. 5A to 5C show other example of display of the ultrasonic testing waveforms by the ultrasonic testing waveform display unit shown in FIG. 1A to 1D.
Figure 5B:
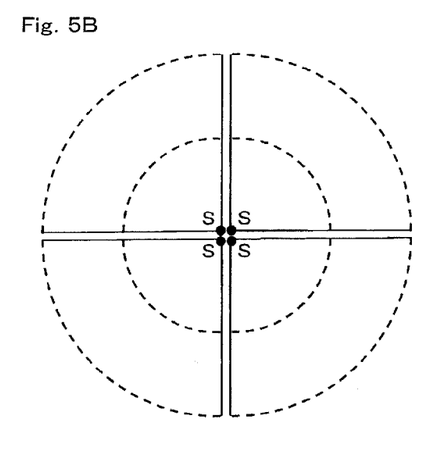
Figure 5C:
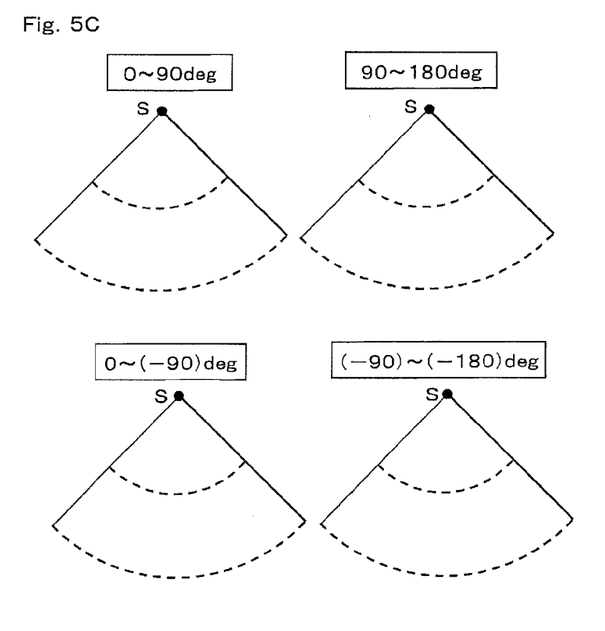

In this embodiment, an example of displaying all the ultrasonic testing waveforms correlated to the propagation direction γ (γ=−180° to)180°) of the ultrasonic wave radially from the identical beginning point S has been described as shown in FIG. 3C and FIGS. 4A and 4B. However, the present invention is not limited thereto, but it is permissible to divide the propagation direction γ (γ=−180° to 180°) of the ultrasonic wave to a plurality of areas as shown in FIGS. 5A to 5C so as to display the ultrasonic testing waveforms radially from different beginning points S on the display in the respective areas.

Hereinafter, the mechanical section 4 for running the ultrasonic probe 1 on the external surface of the pipe P for scanning will be described with reference to FIGS. 6A to 6C. The mechanical section 4 is constructed to be able to obtain a high reliability flaw detection result without any change in the posture of the ultrasonic probe 1 with respect to the pipe P when the ultrasonic probe 1 is run manually for scanning to detect for any flaw. The reason is that if the transducer 11 designed to transmit and receive the ultrasonic wave at the propagation angle γ, for example, 0° happens to transmit and receive the ultrasonic wave at other propagation angle γ due to the change in the posture of the ultrasonic probe 1, the flaw detection accuracy is deteriorated and the flaw tilted angle cannot be evaluated accurately.

Figure 6A:
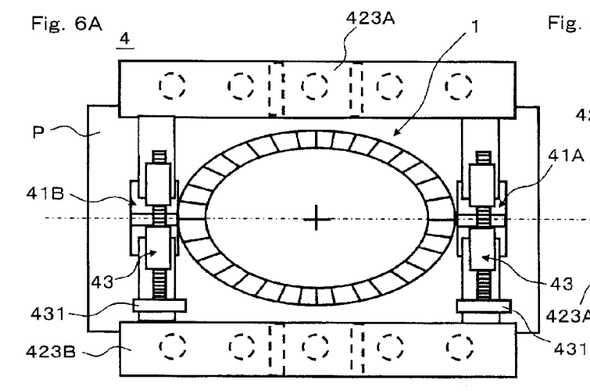
FIG. 6A is a plan view thereof.
Figure 6B:
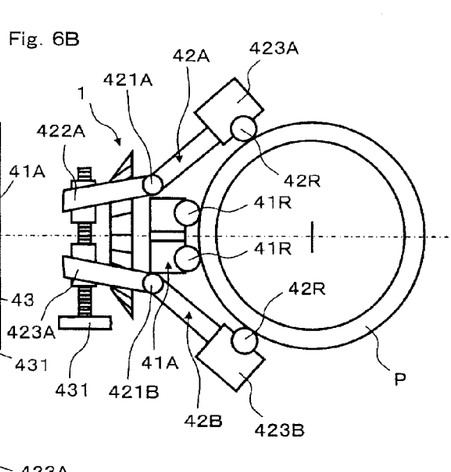
FIG. 6B is a side view thereof and FIG. 6C is a rear view thereof.
Figure 6C:
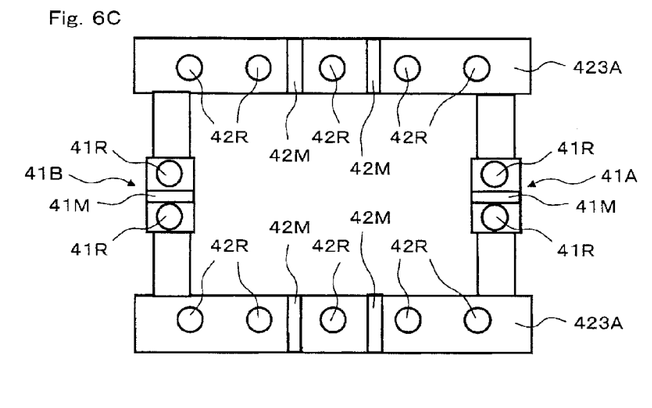

FIGS. 6A to 6C are schematic views each showing the schematic configuration of a structure around the mechanical section 4 possessed by the ultrasonic testing equipment 100. FIG. 6A shows a plan view thereof, FIG. 6B shows a side view thereof and FIG. 6C shows a rear view thereof. In the meantime, FIG. 6C shows only the mechanical section 4.

As shown in FIGS. 6A to 6C, the mechanical section 4 of this embodiment includes a pair of follow-up mechanisms 41A, 41B and a pair of arm mechanisms 42A, 42B.

The pair of follow-up mechanisms 41A, 41B are arranged along the axial direction of the pipe P such that the ultrasonic probe 1 is sandwiched, and are connected to the ultrasonic probe 1 through any appropriate member (not shown). The follow-up mechanisms 41A, 41B have at least one rolling roller 41R which rolls in contact with the external surface of the pipe P. The follow-up mechanism 41A, 41B of this embodiment are arranged to sandwich the center (gravity center) of the ultrasonic probe 1 and have a pair of rolling rollers 41R which roll in contact with the external surface of the pipe P. Although in this embodiment, a spherical bearing capable of rolling in every direction is used as the rolling roller 41R, the present invention is not limited to this example, but it is permissible to employ such as an omni wheel which can roll in two axial directions, sold by, for example, Tosa Denshi.

The ultrasonic probe 1 is placed on the external surface of the pipe P via the pair of rolling rollers 41R (four rolling rollers 41R) possessed by each of the pair of follow-up mechanisms 41A, 41B and can scan the external surface of the pipe P with a distance between the external surface of the pipe P and the ultrasonic probe 1 kept constant by rolling the rolling rollers 41R. Although the four rollers are used as the rollers 41R in this embodiment, the present invention is not limited to this example, but there is no problem even if each follow-up mechanism 41A, 41B has one rolling roller 41R each, because the distance between the external surface of the pipe P and the ultrasonic probe 1 can be kept constant. In the meantime, preferably, the ultrasonic probe 1 and the follow-up mechanisms 41A, 41B are connected to each other under a positional relationship that the position of the center O of the aforementioned spheroid is in the vicinity of the external surface of the pipe P.

The follow-up mechanisms 41A, 41B of this embodiment have a permanent magnet 41M between the pair of rolling rollers 41R as a preferable configuration. If the pipe P has magnetism, absorption force of the permanent magnet 41M contributes to holding the posture of the ultrasonic probe 1 with respect to the pipe P constant.

The ultrasonic probe 1 and the follow-up mechanisms 41A, 41B coupled via the aforementioned appropriate members are installed to an appropriate frame (not shown). Preferably, the ultrasonic probe 1 and the follow-up mechanisms 41A, 41B are installed to the frame so that they can be moved integrally in the diameter direction of the pipe P.

The pair of arm mechanisms 42A, 42B are formed into a substantially U-shape in a plan view and are arranged along the circumferential direction of the pipe P so that the ultrasonic probe 1 and the follow-up mechanisms 41A, 41B are sandwiched, and are connected to the ultrasonic probe 1. More specifically, rotation shafts 421A, 421B of the respective arm mechanisms 42A, 42B are installed to the aforementioned frames rotatably. The ultrasonic probe 1 and the follow-up mechanisms 41A, 41B coupled via the appropriate members are installed to this frame as described above. With the above-described structure, the pair of arm mechanisms 42A, 42B are connected to the ultrasonic probe 1.

The pair of arm mechanism 42A, 42B are constructed so that an interval between them can be adjusted. More specifically, a ball screw mechanism 43 is installed on each of end portions 422A, 422B of the respective arm mechanisms 42A, 42B. By turning an adjustment knob 431 of the ball screw mechanism 43, the end portions 422A, 422B of the respective arm mechanisms 42A, 42B approach or leave each other. Consequently, the respective arm mechanisms 42A, 42B rotate around the rotation shafts 421A, 421B as a reference so that other end portions 423A, 423B of the respective arm mechanisms 42A, 42B approach or leave each other. As described above, the interval between the pair of arm mechanism 42A and 42B can be adjusted.

Each of the arm mechanisms 42A, 42B has at least one pair (five in this embodiment) of the rolling rollers 42R that are arranged to sandwich the center (gravity center) of the ultrasonic probe 1 and roll in contact with the external surface of the pipe P. The rolling rollers 42R are installed to the other end portions 423A, 423B of the arm mechanisms 42A, 42B. Although this embodiment employs the spherical bearing as the rolling roller 42R, it is permissible to use other means similar to the rolling roller 41R. Further, the arm mechanisms 42A, 42B of this embodiment have permanent magnets 42M between the three rolling rollers 42R arranged in the central portion as a preferred structure like the follow-up mechanisms 41A, 41B.

By adjusting the interval between the pair of arm mechanisms 42A and 42B having the above-described structure, the pipe P is sandwiched from the circumferential direction by the pair of arm mechanisms 42A, 42B. Consequently, the posture of the ultrasonic probe 1 connected to the pair of arm mechanisms 42A, 42B with respect to the pipe P can be kept constant. Because the respective arm mechanisms 42A, 42B have the rolling rollers 42R, the rollers 42R are rotated to allow the ultrasonic probe 1 to scan along the external surface of the pipe P, even if the pipe P is sandwiched from the circumferential direction by the pair of arm mechanisms 42A, 42B.

In the meantime, the arm mechanisms 42A, 42B are installed to the frame so that they do not move in the diameter direction of the pipe P. Thus, if the ultrasonic probe 1 and the follow-up mechanisms 41A, 41B are installed to the frame so that they can move integrally in the diameter direction of the pipe P as a preferred structure as described above, the ultrasonic probe 1 and the follow-up mechanisms 41A, 41B can move relative to the arm mechanisms 42A, 42B in the diameter direction of the pipe P. Consequently, even if the external surface of the pipe P is slightly deformed or not circular, the ultrasonic probe 1 and the follow-up mechanisms 41A, 41B are moved in the diameter direction of the pipe P along the external surface of the pipe P with the posture of the ultrasonic probe 1 kept constant when the pipe P is sandwiched from the circumferential direction by the pair of arm mechanisms 42A, 42B. Consequently, it is possible to keep such a positional relationship that the position of the center O of the spheroid is in the vicinity of the external surface of the pipe P.

Further, the mechanical section 4 of this embodiment is constructed so that liquid coupling medium such as water is filled between the ultrasonic probe 1 and the steel pipe P. Alternatively, if any acoustic wedge made of resin or the like exists on the bottom face of the ultrasonic probe 1, the mechanical section 4 is constructed so that coupling medium such as water is filled between this acoustic wedge and the steel pipe P.

In the ultrasonic testing equipment 100 having the mechanical section 4 described above, the posture of the ultrasonic probe 1 with respect to the pipe P is not changed, thereby obtaining a high reliability flaw detection result.

Figure 7:
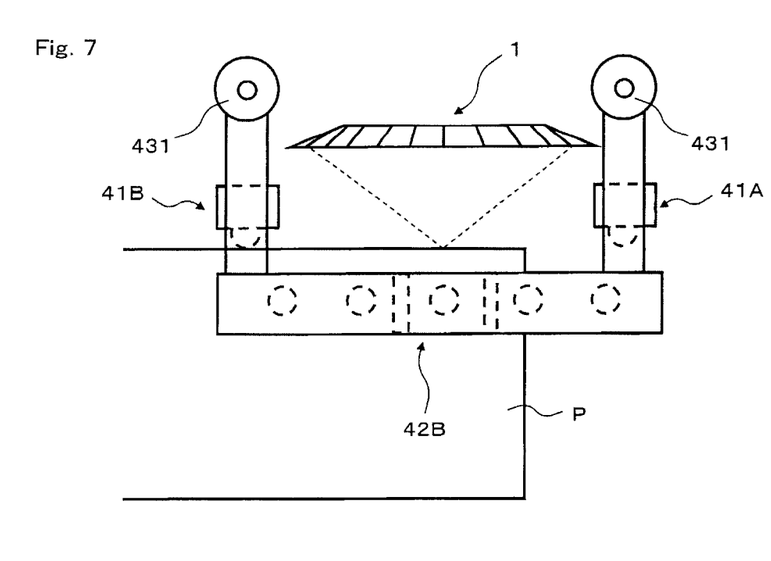
FIG. 7 is a front view for explaining a condition under which a pipe end is detected for any flaw using the ultrasonic testing equipment shown in FIGS. 6A to 6C.

By employing the mechanical section 4 of this embodiment, up to end portions of the pipe P can be detected for any flaw as shown in FIG. 7. That is, even if one side follow-up mechanism 41A is moved beyond an end of the pipe P, up to the end portion of the pipe P can be detected for any flaw because the ultrasonic probe 1 can be held on the external surface of the pipe P by the pair of arm mechanisms 42A, 42B and the other side follow-up mechanism 41B.

Table 1 shows a result of evaluation on the reproducibility of flaw detection when manually detecting flaws generated by discharge processing on a steel pipe using the ultrasonic testing equipment 100 described above.

TABLE 1

| | Tilt angle of flaw with respect to pipe axial direction (deg) | | | | |
|---|---|---|---|---|---|
| | 0 | 30 | 45 | 60 | 90 |
| Reproducibility (db) | 1.2 | 2.0 | 0.9 | 2.0 | 1.6 |

Detection of the flaws under an excellent reproducibility was secured as shown in Table 1.

In the meantime, the ultrasonic probe which employs the mechanical section 4 of this embodiment is not limited to the ultrasonic probe 1 shown in FIGS. 1A to 1D. The mechanical section 4 of this embodiment is applied preferably to an ultrasonic probe A for vertical flaw detection as shown in FIGS. 8A to 8C and an ultrasonic probe 1A having four ultrasonic probes B to E for oblique flaw detection.

Figure 8A:
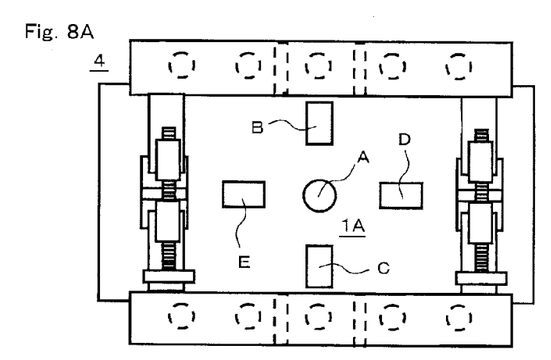
FIG. 8A shows a plan view thereof.
Figure 8B:
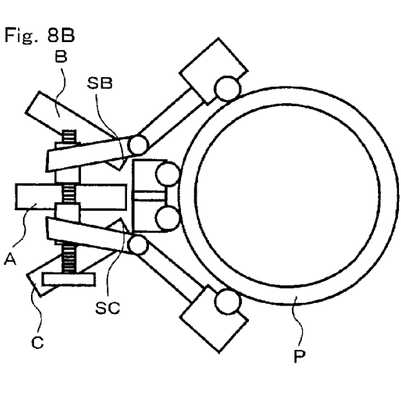
FIG. 8B shows a side view thereof and FIG. 8C shows a front view thereof.
Figure 8C:
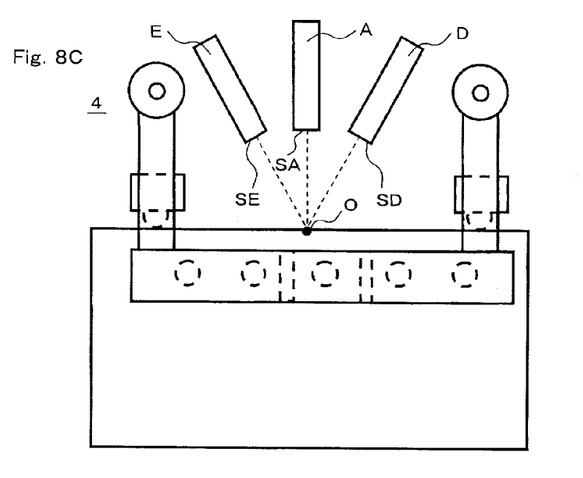

As shown in FIGS. 8A to 8C, four ultrasonic probes B to E are arranged along an annular curved surface obtained by cutting vibration surface SB to SE with two parallel planes facing to each other that do not pass through the center O of a predetermined spheroid and do not sandwich the center O of the spheroid, the two parallel planes being orthogonal to the rotational axis of the spheroid, like the transducer 11 of the aforementioned ultrasonic probe 1. Then, the shape of this annular curved surface is determined so that the external refraction angles of the ultrasonic waves propagated from the respective ultrasonic probes B to E are approximately equivalent and/or the internal refraction angles of the ultrasonic wave are approximately equivalent.

The ultrasonic probe A is arranged such that its vibration surface SA passes through the center O of the spheroid and along a straight line L (corresponding to the rotational axis of the spheroid) orthogonal to the aforementioned two parallel planes (just over the center O of the spheroid in the example shown in FIGS. 8A to 8C). Consequently, there are advantages that oblique flaw detection with the ultrasonic probes B to E is enabled and thickness measurement and lamination detection about the steel pipe P with the ultrasonic probe A are enabled.

Even in the ultrasonic probe 1A described above, if the ultrasonic probe B designed to transmit and receive the ultrasonic wave at the propagation angle γ, for example, 0° happens to transmit and receive the ultrasonic wave at other propagation angle γ because of a change in its posture, the flaw detection accuracy is deteriorated and the tilt angle of the flaw cannot be evaluated accurately. However, by providing with the mechanical section 4 of this embodiment, a high reliability flaw detection result without any change in the posture of the ultrasonic probe 1A with respect to the pipe P can be obtained.

What is claimed is:

1. An ultrasonic testing method comprising the steps of:

arranging an ultrasonic probe having a plurality of transducers arranged along an annular curved surface obtained by cutting a predetermined spheroid with two parallel planes facing to each other that do not pass through the center of the spheroid and do not sandwich the center of the spheroid, the two parallel planes being orthogonal to a rotational axis of the spheroid, so as to face a tubular test object so that a longer axis direction of the annular curved surface is along a longitudinal axial direction of the tubular test object, a shorter axis direction of the annular curved surface is along a circumferential direction of the tubular test object and the center of the spheroid correctly faces to the longitudinal axial center of the tubular test object;

causing transducers appropriately selected from the plurality of the transducers to transmit and receive ultrasonic waves so that the ultrasonic waves are propagated in the tubular test object in a plurality of different propagation directions; and displaying ultrasonic testing waveforms received by the selected transducers radially corresponding to the propagation directions of the ultrasonic waves transmitted and received by the selected transducers, wherein the shape of the annular curved surface is determined so that respective external refraction angles of the ultrasonic wave in the plurality of propagation directions are approximately equivalent and/or respective internal refraction angles of the ultrasonic wave in the plurality of propagation directions are approximately equivalent, wherein in the step of displaying the ultrasonic testing waveforms radially, the ultrasonic testing waveforms are displayed radially with a point of time corresponding to an echo on an incident point of the ultrasonic wave to the tubular test object contained in the ultrasonic testing waveform as a beginning point, and circles indicating points of time corresponding to the echoes on the internal surface and/or the external surface of the tubular test object around the beginning point are displayed.

2. An ultrasonic testing equipment comprising:

an ultrasonic probe having a plurality of transducers arranged along an annular curved surface obtained by cutting a predetermined spheroid with two parallel planes facing to each other that do not pass through the center of the spheroid and do not sandwich the center of the spheroid, the two parallel planes being orthogonal to a rotational axis of the spheroid, the ultrasonic probe being arranged so as to face a tubular test object so that a longer axis direction of the annular curved surface is along a longitudinal axial direction of the tubular test object, a shorter axis direction of the annular curved surface is along a circumferential direction of the tubular test object and the center of the spheroid correctly faces to the longitudinal axial center of the tubular test object;

a transmission/reception control unit that causes at least two transducers selected from the plurality of the transducers to transmit the ultrasonic waves to and receive the same from the tubular test object; and a ultrasonic testing waveform display unit that displays ultrasonic testing waveforms received by the selected transducers radially corresponding to the propagation directions of the ultrasonic waves transmitted and received by the selected transducers, wherein the ultrasonic testing waveform display unit displays the ultrasonic testing waveforms radially with a point of time corresponding to an echo on an incident point of the ultrasonic wave to the tubular test object contained in the ultrasonic testing waveform as a beginning point and displays circles indicating points of time corresponding to the echoes on the internal surface and/or the external surface of the tubular test object around the beginning point.

* * * * *